(12) United States Patent
Huang et al.

(10) Patent No.: US 11,219,359 B2
(45) Date of Patent: *Jan. 11, 2022

(54) ENDOSCOPE SYSTEM

(71) Applicant: Covidien LP, Mansfield, MA (US)

(72) Inventors: Desheng Huang, Shanghai (CN); Ruoxi Sun, Shanghai (CN); Wei Zhang, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/444,241

(22) Filed: Jun. 18, 2019

(65) Prior Publication Data
US 2019/0298155 A1    Oct. 3, 2019

Related U.S. Application Data

(62) Division of application No. 14/729,664, filed on Jun. 3, 2015, now Pat. No. 10,952,600.
(Continued)

(51) Int. Cl.
*A61B 1/12* (2006.01)
*A61B 1/00* (2006.01)
(Continued)

(52) U.S. Cl.
CPC ............ *A61B 1/128* (2013.01); *A61B 1/0008* (2013.01); *A61B 1/0676* (2013.01);
(Continued)

(58) Field of Classification Search
CPC ............. A61B 1/00066; A61B 1/0008; A61B 1/00096; A61B 1/00163; A61B 1/00174;
(Continued)

(56) References Cited

U.S. PATENT DOCUMENTS 6,204,523 B1    3/2001    Carey et al.
6,260,994 B1    7/2001    Matsumoto et al.
(Continued)

FOREIGN PATENT DOCUMENTS

CN    1794944 A    6/2006
EP    1911389 A1    4/2008
(Continued)

OTHER PUBLICATIONS

Partial European Search Report corresponding to EP 15 17 6036.0 dated Nov. 25, 2015.
(Continued)

*Primary Examiner* — Ryan N Henderson
*Assistant Examiner* — Pamela F Wu (57) ABSTRACT

An endoscope system includes an endoscope, a display device, and a cable interconnecting the endoscope and the display device. The endoscope includes an elongated body extending distally from a handle. An image sensor is disposed within a distal portion of the elongated body, a lens is disposed at a distal end of the elongated body, and a light source including one or more light emitting elements is integrated into the distal end of the elongated body and positioned radially outward of the lens. An integrated processor is disposed within the handle.

19 Claims, 5 Drawing Sheets

Related U.S. Application Data (60) Provisional application No. 62/022,835, filed on Jul. 10, 2014.

(51) Int. Cl.
*A61B 1/06* (2006.01)
*A61B 1/05* (2006.01)
*G02B 23/24* (2006.01)

(52) U.S. Cl.
CPC ........ *A61B 1/0684* (2013.01); *A61B 1/00006* (2013.01); *A61B 1/00009* (2013.01); *A61B 1/00016* (2013.01); *A61B 1/00036* (2013.01); *A61B 1/00066* (2013.01); *A61B 1/05* (2013.01); *G02B 23/243* (2013.01); *G02B 23/2423* (2013.01); *G02B 23/2461* (2013.01)

(58) Field of Classification Search
CPC ............ A61B 1/00177; A61B 1/00179; A61B 1/00181; A61B 1/00183; A61B 1/04; A61B 1/05; A61B 1/051; A61B 1/053; A61B 1/055; A61B 1/06; A61B 1/0607; A61B 1/0615; A61B 1/0623; A61B 1/063; A61B 1/0638; A61B 1/0661; A61B 1/0676; A61B 1/0684; A61B 1/12; A61B 1/128; A61B 1/0002; A61B 1/00004; A61B 1/00006; A61B 1/00009; A61B 1/00011; A61B 1/00018; A61B 1/00025; A61B 1/00027; A61B 1/00032; A61B 1/00034; A61B 1/00039; A61B 1/00112; A61B 1/00016; G02B 23/2423; G02B 23/243; G02B 23/2438; G02B 23/2446; G02B 23/2461; G02B 23/2476; G02B 23/2484; G02B 23/2492; G02B 23/2453
USPC ................ 600/109–110, 112, 129–130, 160, 600/175–178

See application file for complete search history.

(56) References Cited

U.S. PATENT DOCUMENTS

| | | | |
|---|---|---|---|
| 6,331,156 B1 | 12/2001 | Haefele et al. | |
| 6,449,006 B1 | 9/2002 | Shipp | |
| 6,488,619 B1 | 12/2002 | Miyanaga | |
| 6,533,722 B2 | 3/2003 | Nakashima | |
| 6,569,088 B2 | 5/2003 | Koshikawa | |
| 6,627,333 B2 | 9/2003 | Hatwar | |
| 6,656,112 B2 | 12/2003 | Miyanaga | |
| 6,696,703 B2 | 2/2004 | Mueller-Mach et al. | |
| 6,796,939 B1 | 9/2004 | Hirata et al. | |
| 6,918,693 B2 | 7/2005 | Ota et al. | |
| 6,921,920 B2 | 7/2005 | Kazakevich | |
| 7,119,376 B1 | 10/2006 | Liu et al. | |
| 7,183,577 B2 | 2/2007 | Mueller-Mach et al. | |
| 7,275,931 B2 | 10/2007 | Katsuda et al. | |
| 7,413,543 B2 | 8/2008 | Banik et al. | |
| 7,442,167 B2 | 10/2008 | Dunki-Jacobs et al. | |
| 7,488,088 B2 | 2/2009 | Brukilacchio | |
| 7,635,330 B2 | 12/2009 | Kang et al. | |
| 7,668,450 B2 | 2/2010 | Todd et al. | |
| 7,691,056 B2 | 4/2010 | Hirata | |
| 7,749,160 B2 | 7/2010 | Hirata | |
| 7,914,448 B2 * | 3/2011 | Bob ................... | H05K 7/20281 600/175 |
| 7,931,587 B2 | 4/2011 | Koshino | |
| 7,968,901 B2 | 6/2011 | Yamashita et al. | |
| 7,976,459 B2 | 7/2011 | Laser | |
| 8,029,439 B2 | 10/2011 | Todd et al. | |
| 8,043,211 B2 | 10/2011 | Hirata | |
| 8,246,230 B2 | 8/2012 | Todd et al. | |
| 8,400,500 B2 | 3/2013 | Hirata | |
| 8,449,457 B2 | 5/2013 | Aizenfeld et al. | |
| 8,480,566 B2 | 7/2013 | Farr | |
| 8,485,966 B2 | 7/2013 | Robertson | |
| 8,556,806 B2 | 10/2013 | Farr | |
| 8,591,408 B2 | 11/2013 | St. George et al. | |
| 8,622,896 B1 | 1/2014 | Termanini | |
| 8,790,253 B2 | 7/2014 | Sunagawa et al. | |
| 8,801,255 B2 | 8/2014 | Kudo | |
| 2002/0184122 A1* | 12/2002 | Yamaguchi ............ | G06Q 40/12 705/30 |
| 2005/0075538 A1 | 4/2005 | Banik et al. | |
| 2006/0063976 A1* | 3/2006 | Aizenfeld ................ | A61B 1/31 600/179 |
| 2007/0173695 A1 | 7/2007 | Hirata | |
| 2007/0197873 A1 | 8/2007 | Birnkrant | |
| 2007/0225556 A1 | 9/2007 | Ortiz et al. | |
| 2007/0249904 A1 | 10/2007 | Amano et al. | |
| 2008/0045800 A2 | 2/2008 | Farr | |
| 2008/0158349 A1* | 7/2008 | Miller ................... | A61B 1/0684 348/82 |
| 2008/0200758 A1 | 8/2008 | Orbay et al. | |
| 2009/0058997 A1 | 3/2009 | Kato | |
| 2009/0076329 A1* | 3/2009 | Su ........................ | A61B 1/0008 600/134 |
| 2009/0154192 A1 | 6/2009 | Krattiger | |
| 2009/0247828 A1 | 10/2009 | Watanabe et al. | |
| 2010/0188493 A1 | 7/2010 | Kanzaki et al. | |
| 2011/0009694 A1 | 1/2011 | Schultz et al. | |
| 2011/0092772 A1 | 4/2011 | Weber et al. | |
| 2011/0112361 A1* | 5/2011 | Ishigami ............ | A61B 1/00052 600/109 |
| 2011/0257481 A1* | 10/2011 | Ogawa ................ | G02B 23/2484 600/109 |
| 2012/0041267 A1 | 2/2012 | Benning et al. | |
| 2012/0320581 A1* | 12/2012 | Rogers .................... | H01L 24/24 362/235 |
| 2013/0131451 A1* | 5/2013 | Dillinger ............... | A61B 1/0011 600/127 |
| 2013/0265798 A1 | 10/2013 | Kudo | |
| 2013/0285094 A1 | 10/2013 | Hsu et al. | |
| 2013/0300847 A1 | 11/2013 | Hashimoto | |
| 2013/0334577 A1 | 12/2013 | Ahn | |
| 2014/0142384 A1* | 5/2014 | Chung ................. | A61B 1/0008 600/112 |
| 2014/0316198 A1* | 10/2014 | Krivopisk .......... | A61B 1/00181 600/109 |
| 2014/0330081 A1 | 11/2014 | Imai | |
| 2015/0297069 A1 | 10/2015 | Coppersmith et al. | |

FOREIGN PATENT DOCUMENTS

| | | |
|---|---|---|
| JP | 2008117184 A | 5/2008 |
| WO | 2010123858 A2 | 10/2010 |
| WO | 2014004992 A1 | 1/2014 |

OTHER PUBLICATIONS

Extended European Search Report corresponding to counterpart Int'l Appln. No. EP 15 17 6036.0, dated May 6, 2016.
European Office Action corresponding to counterpart Int'l Appln. No. EP 15 17 6036.0 dated Apr. 26, 2017.
Chinese First Office Action corresponding to counterpart Int'l Appln. No. CN 201510405306 dated Dec. 5, 2017.
Chinese Second Office Action corresponding to counterpart Patent Application CN 201510405306 dated Jul. 31, 2018.
Australian Examination Report No. 1 corresponding to counterpart Patent Application AU 2015203154 dated Mar. 13, 2019.
Chinese First Office Action dated Mar. 31, 2021 corresponding to counterpart Patent Application CN 201910299060.0.

* cited by examiner

ENDOSCOPE SYSTEM

CROSS-REFERENCE TO RELATED APPLICATIONS

This application is a divisional application of U.S. patent application Ser. No. 14/729,664, filed on Jun. 3, 2015, which claims the benefit of and priority to U.S. Provisional Patent Appl. Ser. No. 62/022,835, filed on Jul. 10, 2014, the entire contents of each of which are incorporated by reference herein.

TECHNICAL FIELD

The present disclosure relates to endosurgical devices and systems for observing internal features of a body during minimally invasive surgical procedures, and more particularly, to endoscope systems and the like.

BACKGROUND

Endoscopes are introduced through an incision or a natural body orifice to observe internal features of a body. Conventional endoscopes include a light transmission pathway, including a fiber guide, for transmitting light from an external light source through the endoscope to illuminate the internal features of the body. Conventional endoscopes also include an image retrieval pathway for transmitting images of these internal features back to an eyepiece or external video system for processing and display on an external monitor.

SUMMARY

The present disclosure is directed to endoscopes and endoscope systems having a light source and camera integrated into a distal end portion of the endoscopes and an integrated processor disposed within a handle of the endoscopes for controlling the endoscope systems.

According to an aspect of the present disclosure, an endoscope includes a handle and an elongated body extending distally from the handle. The elongated body includes a distal portion terminating at a distal end. An image sensor is disposed within the distal portion of the elongated body; a lens is disposed at the distal end of the elongated body, and a light source including one or more light emitting elements is integrated into the distal end of the elongated body and positioned radially outward of the lens. In embodiments, the light emitting elements are disposed in a crescent shape around a portion of the lens. The light emitting elements may be LEDs. The image sensor may be a backside illuminated sensor. In embodiments, the image sensor is a high definition CMOS sensor. The lens may be a focus free lens.

The endoscope may include a passive thermal control system. In embodiments, a thermally conductive substrate is affixed to the light source. A heat sink may be placed in contact with the thermally conductive substrate. In some embodiments, a thermally conductive adhesive is disposed between the heat sink and the thermally conductive substrate. In certain embodiments, the heat sink is cylindrical in shape and positioned in full contact with a cylindrical wall of the elongated body.

In embodiments, the endoscope includes a processor disposed within the handle. The processor includes a system controller, an imaging subsystem, a video processing subsystem, and peripheral controllers for transmitting data to and from external devices, such as the image sensor and the light source. In embodiments, the processor is a system-on-chip.

According to another aspect of the present disclosure, an endoscope includes a handle including a handle housing including a grip portion and a control portion. The handle housing defines an inner chamber containing a plurality of circuit boards for powering and controlling the endoscope system. In embodiments, the handle housing includes: a main board including a processor and memory for system control, data capture, image processing, and video output; a power board including an integrated power chip to manage system power; a button board to enable/disable user controls; and a switch board to power the system on and off.

The button board may be positioned in the control portion of the handle and the main board may be positioned in the grip portion of the handle. In embodiments, the power board is disposed in the grip portion of the handle, and in certain embodiments, the switch board is positioned in the grip portion of the handle.

The endoscope may further include an elongated body extending distally from the handle. The elongated body includes a camera including an image sensor disposed in a distal portion of the elongated body and a lens disposed at the distal end of the elongated body. The elongated body also includes a light source disposed at a distal end of the elongated body. The processor includes a peripheral controller for controlling the transmission of data between the processor and the camera and a peripheral controller for controlling the transmission of data between the processor and the light source.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed endoscope and endoscope system is described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. As used herein, the term "subject" refers to a human patient or other animal. The term "clinician" refers to a doctor, nurse, or other care provider and may include support personnel. The term "about" shall be understood as a word of approximation that takes into account relatively little to no variation in a modified term (e.g., differing by less than 2%).

Figure 1:
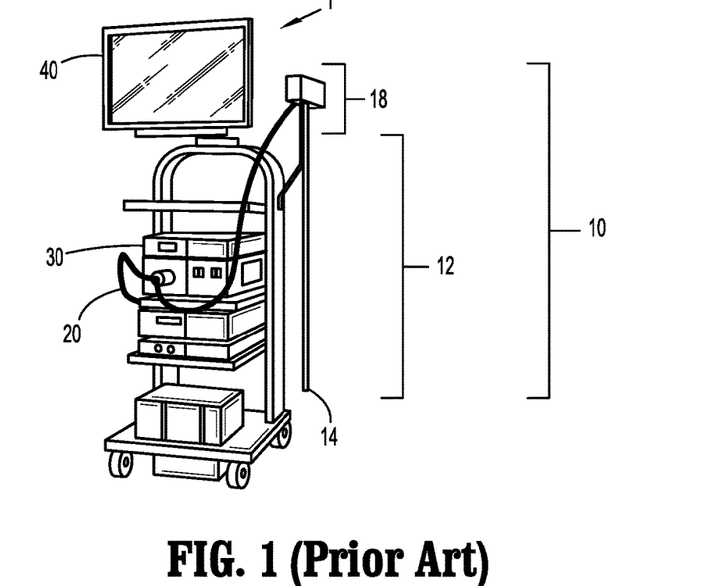
FIG. 1 is a front, perspective view of an endoscope system of the prior art.
Figure 2:
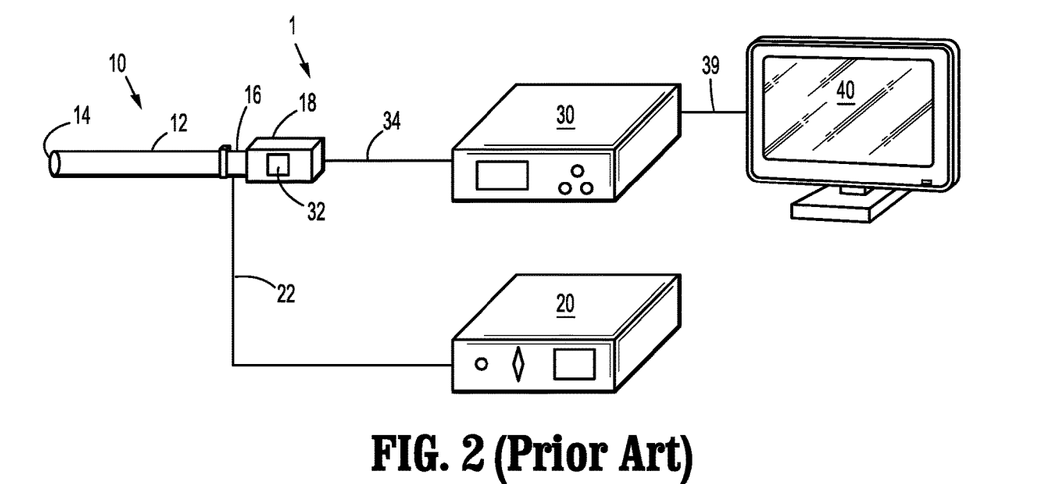
FIG. 2 is front, perspective view illustrating a schematic configuration of the endoscope system of FIG. 1.
Figure 3:
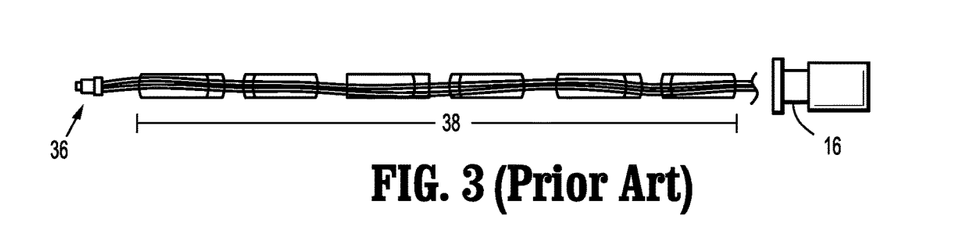
FIG. 3 is a side view illustrating a schematic configuration of an optical system of the endoscope system of FIG. 1.

Referring initially to FIGS. 1-3, a prior art endoscope system 1 includes an endoscope 10, a light source 20, a video system 30, and a display device 40. The light source 20, such as an LED/Xenon light source, is connected to the endoscope 10 via a fiber guide 22 that is operatively coupled to the light source 20 and to an endocoupler 16 disposed on, or adjacent to, a handle 18 of the endoscope 10. The fiber guide 22 includes, for example, fiber optic cable which extends through the elongated body 12 of the endoscope 10 and terminates at a distal end 14 of the endoscope 10. Accordingly, light is transmitted from the light source 20, through the fiber guide 22, and emitted out the distal end 14 of the endoscope 10 toward a targeted internal feature, such as tissue or an organ, of a body of a patient. As the light transmission pathway in such a configuration is long, for example, the fiber guide 22 may be about 1 m to about 1.5 m in length, only about 15% (or less) of the light flux emitted from the light source 20 is outputted from the distal end 14 of the endoscope 10.

The video system 30 is operatively connected to an image sensor 32 mounted to, or disposed within, the handle 18 of the endoscope 10 via a data cable 34. An objective lens 36 is disposed at the distal end 14 of the elongated body 12 of the endoscope 10 and a series of spaced-apart, relay lenses 38, such as rod lenses, are positioned along the length of the elongated body 12 between the objective lens 36 and the image sensor 32. Images captured by the objective lens 36 are forwarded through the elongated body 12 of the endoscope 10 via the relay lenses 38 to the image sensor 32, which are then communicated to the video system 30 for processing and output to the display device 40 via cable 39.

As the image sensor 32 is located within, or mounted to, the handle 18 of the endoscope 10, which can be up to about 30 cm away from the distal end 14 of the endoscope 10, there is loss of image information in the image retrieval pathway as it is difficult to get a high quality image at every point along the whole working distance of the relay lenses 38. Moreover, due to light loss on the relay lenses 38, the objective lens 36 cannot include a small aperture. Therefore, the depth of field is limited and a focusing module (not shown) is typically utilized in the endocoupler 16 to set the objective lens 36 to a desired focal point, which a clinician must adjust when moving the endoscope 10 during a surgical procedure. Also, rotation of the fiber guide 22 will also rotate the relay lenses 38, which changes the viewing angle during use, and the fiber guide 22 also tends to fall due to the force of gravity. Accordingly, a clinician needs to adjust and/or hold the fiber guide 22 during use to keep the view stable, which is inconvenient during operation.

Figure 4:
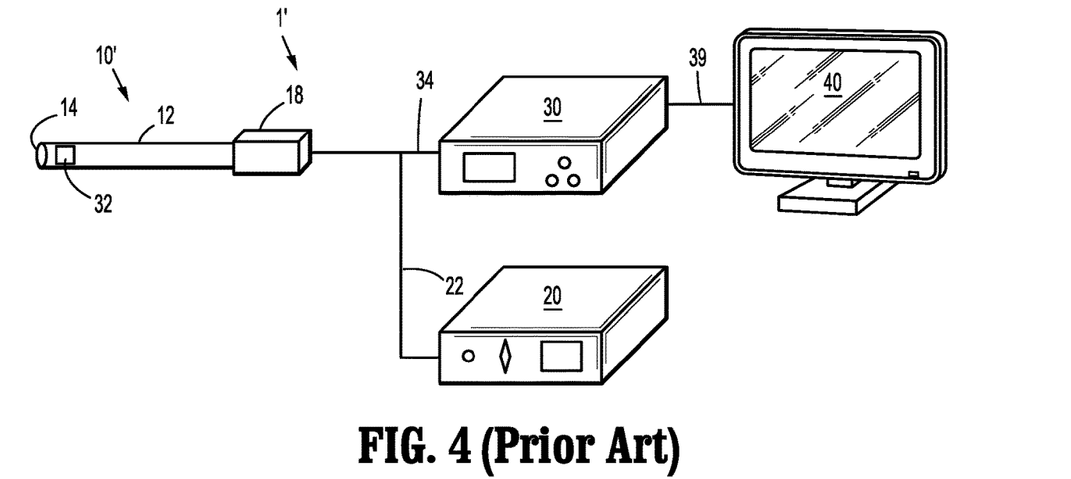
FIG. 4 is a front, perspective view illustrating a schematic configuration of another endoscope system of the prior art.
Figure 5:
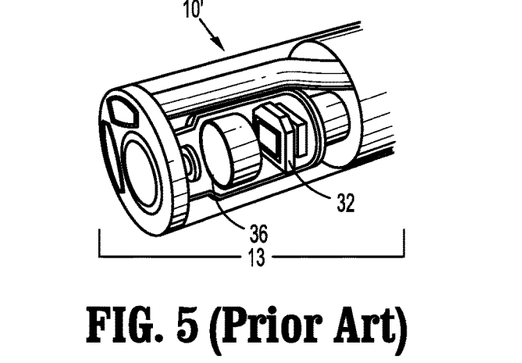
FIG. 5 is a perspective, partial cutaway view illustrating a schematic configuration of a distal end of an endoscope of the endoscope system of FIG. 4.

As shown in FIGS. 4 and 5, another prior art endoscope system 1', which is substantially similar to endoscope system 1 and therefore will only be described with respect to the differences therebetween, includes the image sensor 32 in a distal portion 13 of the elongated body 12 of the endoscope 10' such that the image retrieval pathway between the objective lens 36 and the image sensor 32 is shorter than that of the endoscope system 1. The endoscope system 1' adopts the same light transmission pathway as that of the endoscope system 1 (i.e., from the light source 20 and through the fiber guide 22), and thus light consumption on transmission is still large. However, the fiber guide 22 may be integrated with the data cable 34, thereby making the endoscope 10' easier to operate as a clinician does not need to adjust the fiber guide 22 during use.

Figure 6:
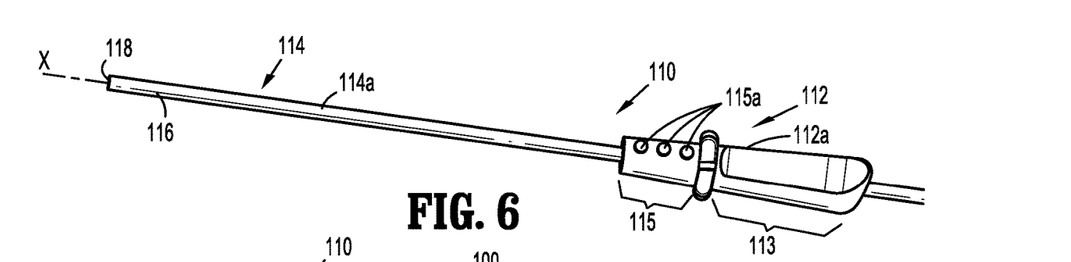
FIG. 6 is a perspective view of an endoscope in accordance with an embodiment of the present disclosure.
Figure 7:
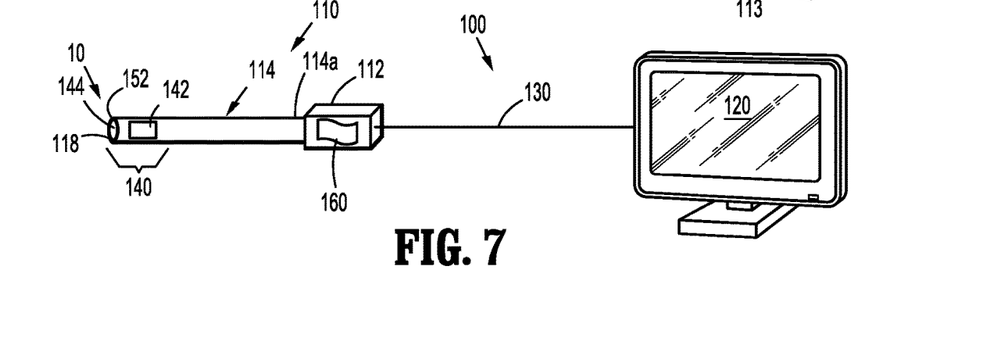
FIG. 7 is a front, perspective view illustrating a schematic configuration of an endoscope system in accordance with an embodiment of the present disclosure.

Referring now to FIGS. 6 and 7, an endoscope system 100 of the present disclosure includes an endoscope 110, a display 120, and a cable 130 connecting the endoscope 110 and the display 120. A camera 140, a light source 150, and an integrated processor 160 are contained within the endoscope 110.

The endoscope 110 includes a handle 112 and an elongated body 114 having a cylindrical wall 114a extending distally from the handle 112 along a longitudinal axis "x." The elongated body 114 includes a distal portion 116 terminating at a distal end or tip 118. The handle 112 includes a handling housing 112a including a grip portion 113 for handling by a clinician and a control portion 115 including actuating elements 115a (e.g., buttons, switches etc.) for functional control of the endoscope 110.

Figure 8:
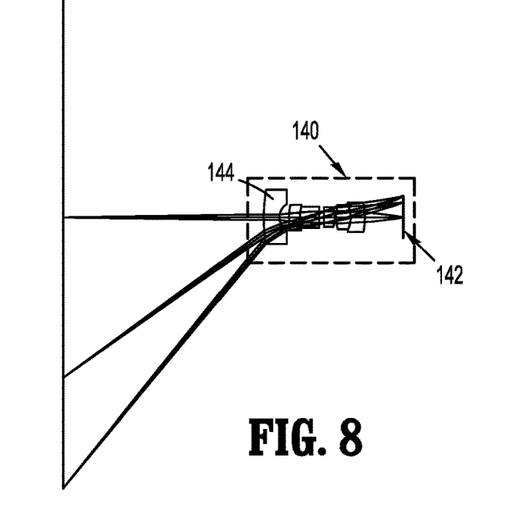
FIG. 8 is a schematic illustration of a camera of the endoscope of FIG. 6.

As shown in FIG. 8, in conjunction with FIG. 7, the camera 140 is disposed within the elongated body 114 of the endoscope 110. The camera 140 includes an image sensor 142 disposed within the distal portion 116 of the elongated body 112 proximal of a lens 144 that is positioned at the distal end 118. The image sensor 142 may be a charge-coupled device (CCD), a complementary metal-oxide-semiconductor (CMOS), or a hybrid thereof. In embodiments, the image sensor 142 is a highly sensitive, backside illuminated sensor (BSI). In embodiments, the lighting flux required by the image sensor 142 may be up to about 20 lm.

As the image retrieval pathway is shortened over that of traditional endoscope systems (e.g., FIG. 1) and the need for relay lenses is eliminated, the depth of field can be expanded and optimized. Accordingly, the lens 144 may include a depth of field from about 20 mm to about 110 mm with optimized image quality and a field-of-view of about 100 degrees. In embodiments, the lens 144 is a focus free lens. As compared to traditional endoscopes, a focus free lens relies on depth of field to produce sharp images and thus, eliminates the need to determine the correct focusing distance and setting the lens to that focal point. Accordingly, the aperture of the lens 144 can be relatively small, taking up less space at the distal end 118 of the elongated body 114. In embodiments, the outer diameter of the lens 144 is up to about 6 mm.

The light source 150 is disposed at the distal end 118 of the endoscope 110. Light source 150 includes one or more high efficiency light emitting elements 152, such as light-emitting diodes (LED). In embodiments, the light emitting elements 152 have a luminous efficacy of up to about 80 lm/W (lumen/watt). As compared to traditional endoscopes, the light source of the present disclosure eliminates the need for the use of an external light source and fiber guide, which can lower the cost of the endoscope system, simplify the endoscope system structure, and reduce light consumption and/or light distortion during light transmission.

Figure 9:
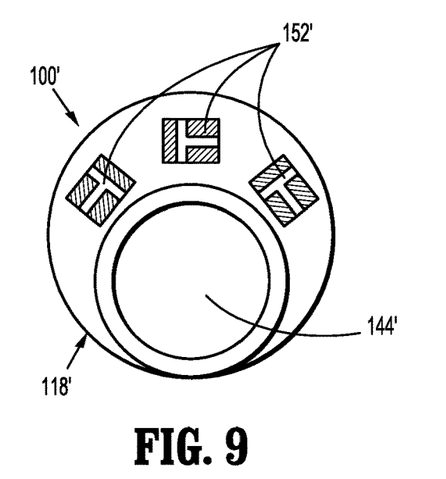
FIG. 9 is an end view illustrating a schematic configuration of a distal end of an endoscope in accordance with an embodiment of the present disclosure.

The light emitting elements 152 are arranged radially outward of the lens 144 at the distal end 118 of the elongated body 114 of the endoscope 110. The light source 150 may include a plurality of individual light emitting elements 152 arranged in an annular ring, such as an LED ring, around the lens 144 (FIG. 7) to ensure adequate and even light distribution. In some embodiments, such as that shown in FIG. 9, a distal end 118' of an endoscope 100' may include a plurality of individual light emitting elements 152' arranged in a crescent or arc shape around a portion of the lens 144'. The dimensional area of the light source 150 at the distal end 118 of the endoscope may be about, or smaller than, 0.4 $cm^2$, with the total light output area being no larger than about 0.1 $cm^2$. To reduce the heat output from such a small area by the high density of light, thermal control is managed by reducing heat generation and/or increasing heat conduction.

Heat generation may be managed, for example, by controlling the luminous efficacy of the light emitting elements 152 and the lighting flux required by the image sensor 142. In embodiments, the endoscope 100 of the present disclosure includes high efficiency LED light emitting elements 152 and a BSI CMOS sensor 142. The BSI CMOS sensor 142 reduces the lighting flux required to get a bright and clear image in a desired body cavity over image sensors utilized in traditional endoscopes. Accordingly, in embodiments where, for example, about 20 lm of lighting flux is required, such as within an abdomen of a patient, the power consumption of LED light emitting elements 152 having a luminous efficacy of about 80 lm/W will be about 0.25 W (20 l m/80 l m/W=0.25 W). As about 80% of the power consumption of an LED is typically turned into heat, an LED light emitting element 152 with 0.25 W power consumption would generate no more than about 0.2 W of heat, which is a relatively very small amount of heat that can be controlled by a passive thermal system.

Figure 10:
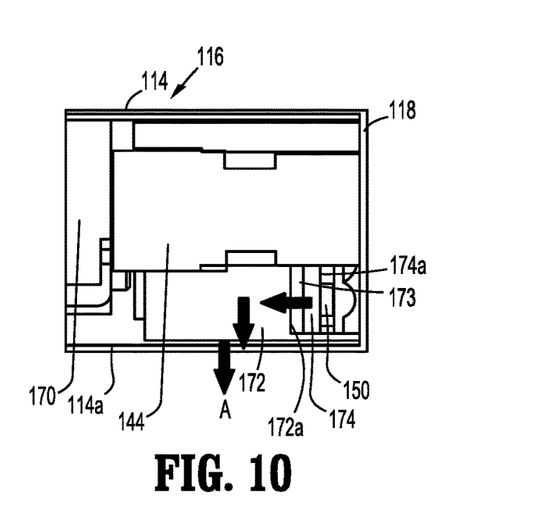
FIG. 10 is a side, cross-sectional view of a distal portion of the endoscope of FIG. 6.
Figure 11:
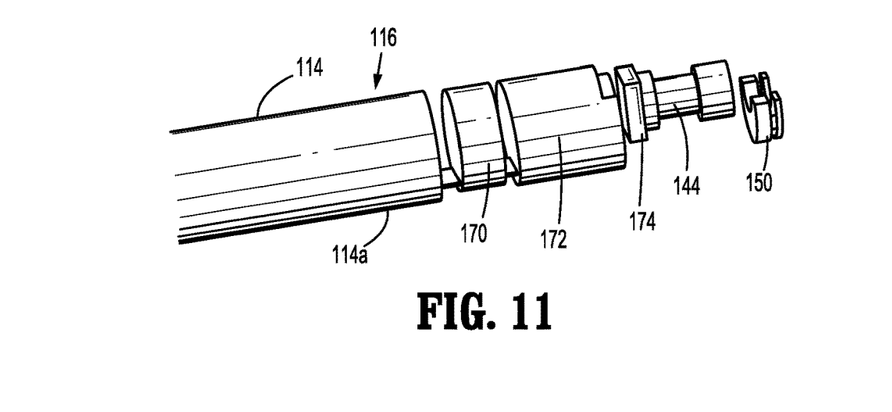
FIG. 11 is a side, perspective view, with parts separated, of the distal portion of the endoscope of FIG. 10.

To increase heat conduction, a passive thermal control system includes a plurality of thermally conductive materials in successive contact with each other so that heat flows from an area of higher temperature to one of lower temperature thereby transporting the excess heat away from the source into the ambient environment. As shown in FIGS. 10 and 11, contained within the cylindrical wall 114a of the endoscope 110 is a fixture 170 for fixing the lens 144 and a heat sink 172 within the distal portion 116 of the elongated body 114, a thermally conductive substrate 174 in contact with a distal side 172a of the heat sink 172, and a light source 150 affixed to a distal side 174a of the thermally conductive substrate 174. Heat generated by the light source 150 is conducted to the thermally conductive substrate 174, the heat sink 172, the cylindrical wall 114a of the elongated body 114, and dissipated into the surrounding air as shown by arrows "A".

In embodiments, a thin coating of a thermally conductive adhesive 173 may be applied to the distal side 172a of the heat sink 172 to increase the heat conduction between the heat sink 172 and the substrate 174. The heat sink 172 may be shaped as a cylinder that is dimensioned to fit within and fully contact the inner surface of the cylindrical wall 114a of the elongated body 114, thereby maximizing the contact area between the heat sink 172 and the cylindrical wall 114a. The profile of the heat sink 172 may be designed to match the lens 144 and the light source 150 so that in addition to conducting heat, the heat sink 172 also aids in fixing the lens 144 and the light source 150 within the elongated body 114.

Figure 12:
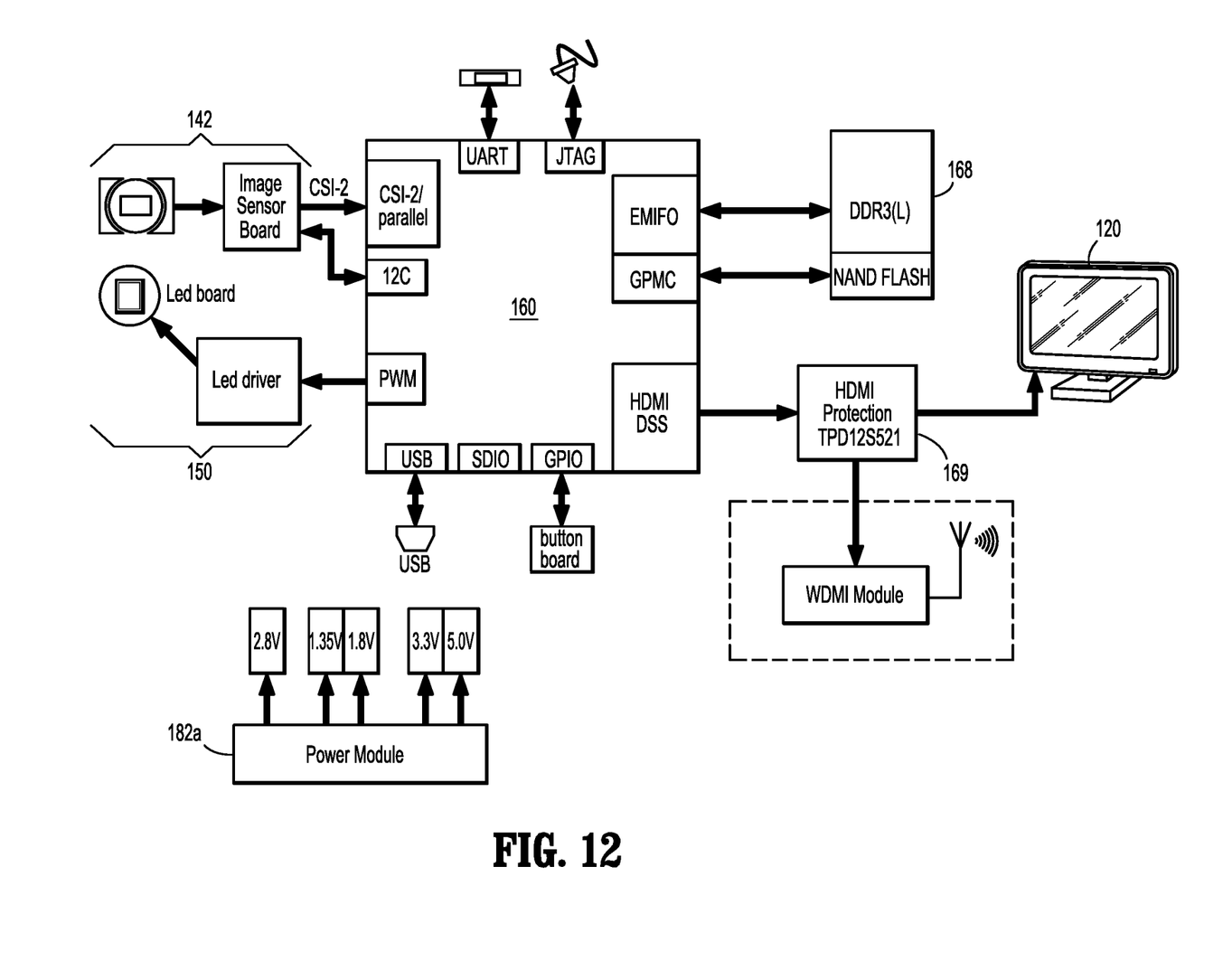
FIG. 12 is a block diagram of system components of the endoscope system of FIG. 7.
Figure 13:
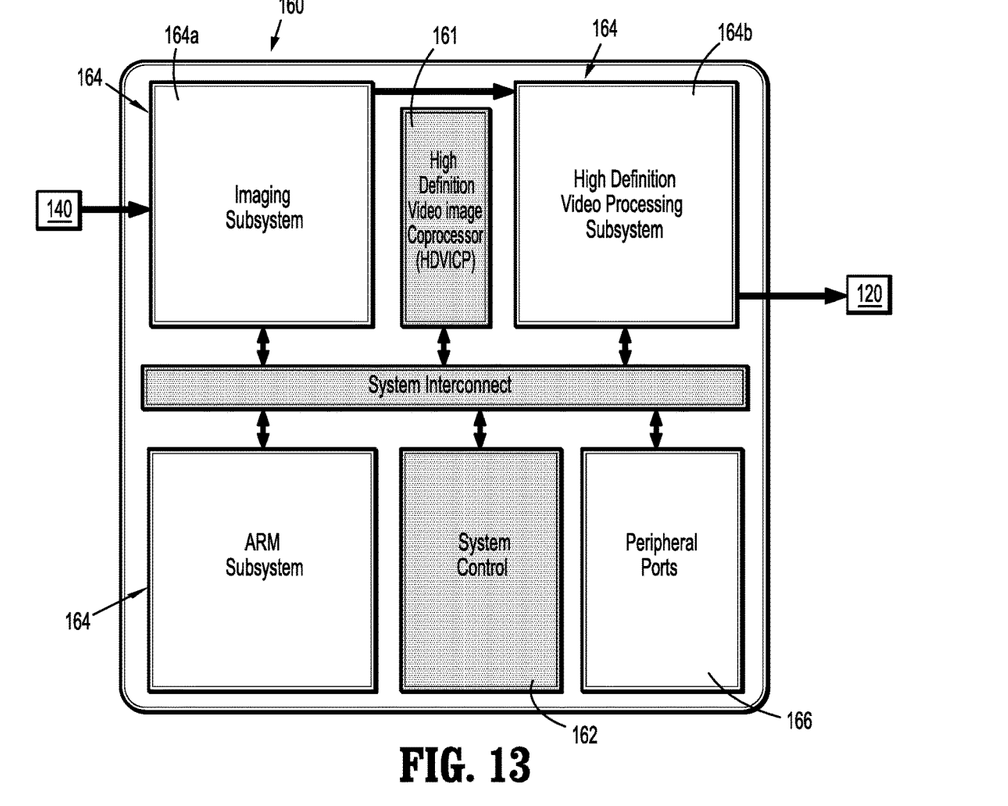
FIG. 13 is a block diagram of an integrated processor of FIGS. 12.

Referring now to FIGS. 12 and 13, the integrated processor 160 is designed for master control of the endoscope system 100. The processor 160 is an integrated circuit including a system controller 162, various subsystems 164, such as an imaging subsystem 164a and a high definition video processing subsystem 164b, and peripherals 166, such as input/output (I/O) interfaces for controlling data transmission to and/or from external devices, such as the image sensor 142, the light source 150, the actuating elements 115a in the control portion 115 of the handle 112, and the display device 120. The processor 160 is also responsible for the configuration and control of memory 168. In embodiments, the processor 160 is a system-on-chip (SoC). Compared to traditional hardware architecture, the power consumption of a SoC is low resulting in less heat generation. Accordingly, thermal control of the endoscope is benefitted from a high level integrated, low power consumption SoC.

The processor 160 is configured and designed to capture Full HD raw data from the camera 140 and to transmit the data to the imaging subsystem 164a for video processing, including, for example, color conversion, defect correction, image enhancement, H3A (Auto White Balance, Auto Exposure, and Auto Focus), and resizer. The data is then transmitted to the high definition video processing subsystem 164b for wrapping of the processed data, and finally to an HDMI output 169 for image display on the display device 120. The hardware modules may be tailored to control power consumption. In embodiments, some hardware functional blocks, such as a high definition video image co-processor 161, and some peripherals 166, such as Ethernet and some I/O interfaces, may be disabled. Such system software optimization of the video pipeline results in lower resource requirements and the tailored hardware modules optimize power consumption for thermal control.

Figure 14:
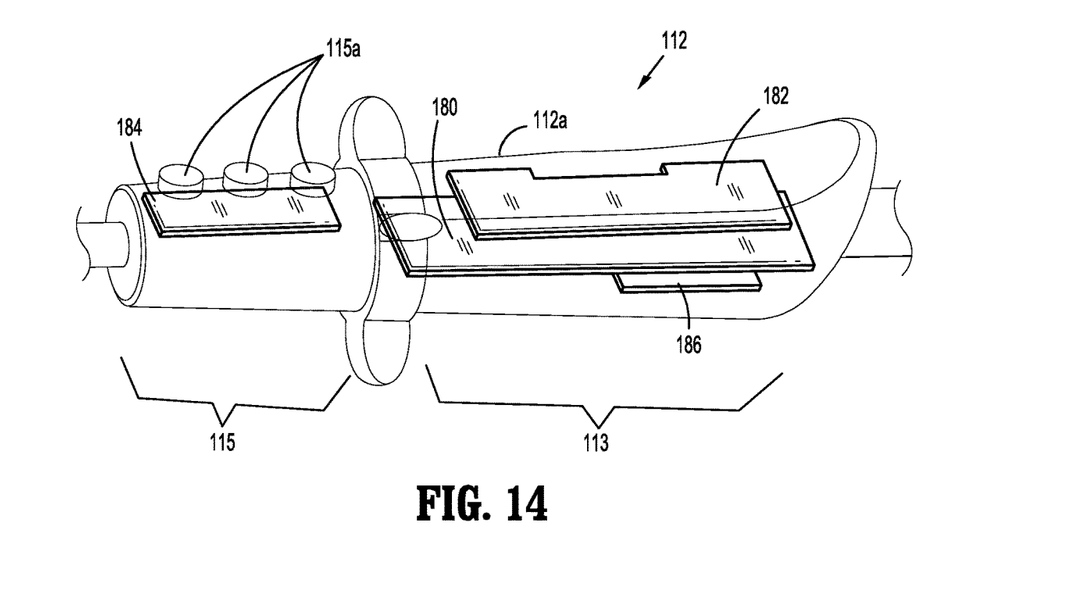
FIG. 14 is a top, perspective view of a handle of the endoscope of FIG. 6.

As shown in FIG. 14, in conjunction with FIGS. 12 and 13, the hardware structure may include multiple circuit boards to maximize the use of the three dimensional space within the handle housing 112a and/or minimize the dimensional size of the handle 112 to a smaller and lightweight construction. The handle 112 defines an inner chamber containing: a main board 180 including the processor 160 and the memory 168 for performing system control, data capture, imaging processing, and video output; a power board 182 including an integrated power chip 182a to manage the system's power; a button board 184 operably associated with the actuating elements 115a of the control portion 115 of the handle 112 for enabling/disabling a user interface on screen display menu, system functional controls and shortcuts; and a switch board 186 for powering the whole system on and off. The cable 130 connecting the endoscope 110 and the display 120 may, in addition to the HDMI data pathway, include a power wire and converter for converting alternating current (e.g., 110/220V AC) into direct current (e.g., 5V DC) for system power.

EXAMPLES

Example 1

An endoscope was constructed which included three high efficiency LEDs having a luminous efficacy of about 80 lm/W and an OV2724 CMOS HD image sensor which is commercially available from OmniVision of Santa Clara, Calif. A passive thermal control system was designed to include the thermally conductive materials provided in Table 1 below.

TABLE 1

Thermal Conductive Materials in a Thermal Control System

| Material | Thermal Conductivity (W/m*K) |
|---|---|
| Ceramic substrate | 320 |
| Silicone thermal adhesive | 2-5 |
| Aluminum heat sink | 230 |
| Stainless steel cylindrical wall | 16 |
| Air | 0.024 |

Example 2

The thermal control of the endoscope of Example 1 was tested by measuring the temperature at the surface of the distal end of the elongated body of the endoscope inside an artificial abdominal cavity having a 298.8K environment temperature after the endoscope was powered-on for 60 minutes. As shown in Table 2 below, the temperature rise was under 10K for a 20 lm flux, which means that the temperature at the distal end of the endoscope was not over about 42° C. during use.

TABLE 2

Temperature Test Results

| Flux (1 m) | Voltage (V) | Current (mA) | Temperature (K) | Temperature rise (K) |
|---|---|---|---|---|
| 7.29 | 7.789 | 10 | 296.23 | 2.48 |
| 11.17 | 7.839 | 15 | 297.26 | 3.56 |
| 14.54 | 7.871 | 20 | 298.52 | 5.31 |
| 18.74 | 7.904 | 25 | 299.88 | 6.13 |
| 22.43 | 7.929 | 30 | 300.78 | 7.03 |
| 26.14 | 7.951 | 35 | 303.88 | 10.13 |

Example 3

The lighting stability of the endoscope of Example 1 was tested by continually working the endoscope for over a 72 hour period under the same test conditions of the temperature test of Example 2. As shown in Table 3 below, the temperature was successfully controlled by the passive thermal control system.

TABLE 3

Stability Test Results

| Flux (1 m) | Voltage (V) | Current (mA) | Time (h, min) |
|---|---|---|---|
| 20.74 | 7.937 | 30 | 0 h 00 min |
| 21.16 | 7.936 | 30 | 4 h 26 min |
| 21.01 | 7.934 | 30 | 5 h 14 min |
| 20.29 | 7.933 | 30 | 22 h 56 min |
| 20.80 | 7.933 | 30 | 29 h 08 min |
| 20.64 | 7.929 | 30 | 50 h 21 min |
| 20.33 | 7.925 | 30 | 74 h 01 min |

It will be understood that various modifications may be made to the embodiments described herein. Therefore, the above description should not be construed as limiting, but merely as exemplifications of various embodiments. Those skilled in the art will envision other modifications within the scope and spirit of the claims appended thereto.

What is claimed is:

1. An endoscope including:
   a handle including a handle housing including a grip portion configured for handling the endoscope and a control portion including actuating elements for functional control of the endoscope, the handle housing defining an inner chamber containing a plurality of circuit boards including:
      a main board including a processor and memory for system control, data capture, image processing, and video output;
      a power board including an integrated power chip to manage system power;
      a button board to enable/disable user controls; and
      a switch board to power the endoscope on and off,
   the main board, the power board, and the switch board positioned in the grip portion of the handle housing, and the button board positioned in the control portion of the handle housing and operably associated with the actuating elements;
   an elongated body extending distally from the control portion of the handle housing, the grip portion and the control portion of the handle extending linearly along a longitudinal axis defined by the elongated body, the elongated body including:
      a camera including an image sensor disposed in a distal portion of the elongated body and a lens disposed at a distal end of the elongated body; and
      a light source disposed at the distal end of the elongated body,
   wherein the processor includes a first peripheral controller for controlling the transmission of data between the processor and the camera and a second peripheral controller for controlling the transmission of data between the processor and the light source; and
   a passive thermal control system including:
      a thermally conductive substrate disposed within the distal portion of the elongated body, the thermally conductive substrate including a distal side affixed to the light source; and
      a heat sink disposed within the distal portion of the elongated body, the heat sink including a distal side coupled to the thermally conductive substrate and an inner surface having a profile matching the lens and the light source.

2. The endoscope of claim 1, wherein the light source includes light emitting elements integrated into the distal end of the elongated body and positioned radially outward of the lens.

3. The endoscope of claim 2, wherein the light emitting elements are disposed in a crescent shape around a portion of the lens.

4. The endoscope of claim 1, wherein the processor is a system-on-chip.

5. The endoscope of claim 1, further comprising a cable extending from the grip portion of the handle, the cable connectable to a display.

6. The endoscope of claim 1, wherein the passive thermal control system includes a thermally conductive adhesive disposed between the heat sink and the thermally conductive substrate.

7. The endoscope of claim 1, wherein the passive thermal control system includes a cylindrical wall of the elongated body, and the heat sink has a cylindrical shape including an outer surface in full contact with an inner surface of the cylindrical wall.

8. The endoscope of claim 1, wherein the main board, the power board, and the switch board extend along parallel axes within the inner chamber of the handle housing.

9. The endoscope of claim 1, wherein the handle includes a collar extending around the handle housing, the control portion of the handle disposed distal to the collar.

10. The endoscope of claim 9, wherein the collar includes a plurality of protrusions extending radially outwardly therefrom.

11. An endoscope comprising:
a handle;
an elongated body extending distally from the handle housing, the elongated body including:
a camera including an image sensor disposed in a distal portion of the elongated body and a lens disposed at a distal end of the elongated body; and
a light source disposed at the distal end of the elongated body; and
a passive thermal control system including:
a thermally conductive substrate disposed within the distal portion of the elongated body, the thermally conductive substrate including a distal side affixed to the light source; and
a heat sink disposed within the distal portion of the elongated body with the thermally conductive substrate disposed within the heat sink, the heat sink including a distal side coupled to the thermally conductive substrate and an inner surface having a profile matching the lens and the light source.

12. The endoscope of claim 11, wherein the heat sink includes an outer surface in full contact with an inner surface of the elongated body.

13. The endoscope of claim 11, wherein the passive thermal control system includes a thermally conductive adhesive disposed between the heat sink and the thermally conductive substrate.

14. The endoscope of claim 11, wherein the passive thermal control system includes a fixture disposed within the elongated body proximal to the lens and the heat sink, a distal surface of the fixture positioned adjacent to the lens.

15. The endoscope of claim 14, wherein the fixture is axially spaced from the heat sink.

16. The endoscope of claim 11, wherein the lens extends proximally through the heat sink.

17. The endoscope of claim 11, wherein the light source includes light emitting elements integrated into the distal end of the elongated body and positioned radially outward of the lens.

18. The endoscope of claim 17, wherein the light emitting elements are disposed in a crescent shape around a portion of the lens.

19. The endoscope of claim 17, wherein the light emitting elements are arranged in an annular ring around the lens.

* * * * *